United States Patent
Kinoshita et al.

(10) Patent No.: US 8,827,926 B2
(45) Date of Patent: Sep. 9, 2014

(54) GUIDE WIRE

(75) Inventors: Yasushi Kinoshita, Shizuoka (JP); Junichi Kobayashi, Shizuoka (JP); Tadashi Kousai, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 106 days.

(21) Appl. No.: 12/343,928

(22) Filed: Dec. 24, 2008

(65) Prior Publication Data
US 2009/0182246 A1 Jul. 16, 2009

Related U.S. Application Data

(60) Provisional application No. 61/006,202, filed on Dec. 31, 2007, provisional application No. 61/024,766, filed on Jan. 30, 2008.

(30) Foreign Application Priority Data

Dec. 28, 2007 (JP) ................................ 2007-340858
Jan. 25, 2008 (JP) ................................ 2008-015575

(51) Int. Cl.
*A61M 25/00* (2006.01)
*A61M 25/098* (2006.01)

(52) U.S. Cl.
USPC ............ 600/585; 604/523; 604/528; 604/529

(58) Field of Classification Search
USPC ........ 600/585; 604/93.01, 264, 523, 528, 529
See application file for complete search history.

(56) References Cited

U.S. PATENT DOCUMENTS

| | | | |
|---|---|---|---|
| 5,253,653 A | 10/1993 | Daigle et al. | |
| 5,379,779 A | 1/1995 | Rowland et al. | |
| 5,460,187 A | 10/1995 | Daigle et al. | |
| 5,465,732 A | 11/1995 | Abele | |
| 5,479,938 A * | 1/1996 | Weier | 600/585 |
| 5,606,981 A * | 3/1997 | Tartacower et al. | 600/585 |
| 5,797,857 A | 8/1998 | Obitsu | |
| 6,620,114 B2 | 9/2003 | Vrba et al. | |

(Continued)

FOREIGN PATENT DOCUMENTS

| | | |
|---|---|---|
| CA | 1324553 C | 11/1993 |
| EP | 0 759 793 B | 3/1997 |

(Continued)

OTHER PUBLICATIONS

Extended European Search Report issued in EP 08 17 2416.3, May 8, 2009, EPO, Munich, DE.

*Primary Examiner* — Devin Henson
(74) *Attorney, Agent, or Firm* — Buchanan, Ingersoll & Rooney PC

(57) ABSTRACT

A guide wire includes an elongated wire body and a radiopaque part capable of forming an X-ray image and located at the distal end portion of the wire body. The radiopaque part has a radiopaque member and a resin coating layer. The radiopaque member is composed of a metallic material capable of forming an X-ray image and arranged outside the wire body and in the lengthwise direction of the wire body. The resin coating layer covers the radiopaque member and at least part of coating layer contains a radiopaque material capable of forming an X-ray image. The radiopaque part is divided into a first radiopaque region, a second radiopaque region, and a third radiopaque region which are sequentially arranged from the distal end in the lengthwise direction of the wire body.

21 Claims, 6 Drawing Sheets

(56) References Cited

U.S. PATENT DOCUMENTS

| | | |
|---|---|---|
| 6,636,758 B2 * | 10/2003 | Sanchez et al. ............... 600/434 |
| 6,673,025 B1 * | 1/2004 | Richardson et al. .......... 600/585 |
| 7,022,086 B2 | 4/2006 | Ehr |
| 7,097,624 B2 * | 8/2006 | Campion et al. .............. 600/585 |
| 2008/0161726 A1 | 7/2008 | Itou |
| 2008/0161727 A1 | 7/2008 | Aimi et al. |
| 2008/0194992 A1 | 8/2008 | Satou et al. |
| 2008/0281230 A1 | 11/2008 | Kinoshita et al. |

FOREIGN PATENT DOCUMENTS

| | | |
|---|---|---|
| JP | 7-28562 U | 5/1995 |
| JP | 2001-346884 A | 12/2001 |
| JP | 2007-135645 A | 6/2007 |
| WO | 95/24237 A2 | 9/1995 |

\* cited by examiner

GUIDE WIRE

This application claims priority under 35 U.S.C. §119(e) to U.S. Provisional Application No. 61/006,202 filed on Dec. 31, 2007, and U.S. Provisional Application No. 61/024,766 filed on Jan. 30, 2008, the entire content of both of which is incorporated herein by reference.

TECHNOLOGICAL FIELD

The disclosure here generally pertains to an elongated medical device. More particularly, the disclosure relates to a guide wire.

BACKGROUND DISCUSSION

A guide wire is used to facilitate insertion of a catheter into a lumen of a living body, such as the digestive tract and a blood vessel. During use, a catheter can be slipped over the guide wire.

A guide wire is also used to lead an endoscope or a catheter inserted into the lumen of an endoscope to a desired position in the lumen of a living body at the time of observation or treatment of the living body lumen. An example of such a guide wire is discussed in Japanese Patent Laid-Open No. 2007-135645.

A guide wire for this purpose includes a long wire and a coil covering the distal end of the wire. The coil may be formed from a radiopaque material such as a noble metal. The coil makes the distal end of the guide wire visible to facilitate insertion of the guide wire into a living body by radioscopy. The coil includes two parts, a first coil and a second coil, and each part is formed from a helically wound wire.

The conventional coil consisting of two parts is observed during radioscopy as one monochromatic continuous member with a certain intensity because the two parts are close to each other. This causes difficulties in locating the distal end of the guide wire being inserted into the lumen of a living body.

Moreover, the conventional coil alone does not produce a high-contrast X-ray image. This causes difficulties in locating the distal end of the guide wire and hence hinders smooth insertion of the guide wire into a living body. The fact that the guide wire is monochromatic and merely provides a low-contrast X-ray image makes it difficult to determine how far the guide wire has advanced and creates difficulties in locating the distal end of the guide wire being inserted into a living body.

SUMMARY

According to one aspect, a guide wire guide wire comprises an elongated wire body and an X-ray producible radiopaque part, wherein the elongated wire body extends in a lengthwise direction, and the radiopaque part is located at the distal end portion of the wire body. The radiopaque part comprises a radiopaque member composed of an X-ray producible metallic material which is adapted to produce an X-ray image. The radiopaque member is arranged outside the wire body and in the lengthwise direction of the wire body. The radiopaque part also comprises a resin coating layer covering the radiopaque member, with at least a part of the resin coating layer that covers the radiopaque member containing an X-ray producible radiopaque material which is adapted to produce an X-ray image. The radiopaque part is divided into at least a first radiopaque region, a second radiopaque region, and a third radiopaque region which are sequentially arranged each immediately after one another in the lengthwise direction of the wire body such that the second radiopaque region is positioned between the first and third radiopaque regions. The radiopaque member is located in each of the first, second and third radiopaque regions, and the second radiopaque region possesses a lesser X-ray image producing capability than the first radiopaque region and the third radiopaque region. The lesser X-ray image producing capability of the second radiopaque region relative to the first radiopaque region being due at least in part to the radiopaque member in the second radiopaque region being arranged less densely than that the radiopaque member in the first radiopaque region, and the resin coating layer in the second radiopaque region containing a lesser amount of the X-ray producible radiopaque material than the resin coating layer in the first radiopaque region.

According to another aspect, a guide wire guide wire comprises an elongated wire body and an X-ray producible radiopaque part, wherein the elongated wire body extends in a lengthwise direction, and the radiopaque part is located at the distal end portion of the wire body. The radiopaque part comprises a radiopaque member composed of an X-ray producible metallic material which is adapted to produce an X-ray image. The radiopaque member is arranged outside the wire body and in the lengthwise direction of the wire body. The radiopaque part also comprises a resin coating layer covering the radiopaque member, with at least a part of the resin coating layer that covers the radiopaque member containing an X-ray producible radiopaque material which is adapted to produce an X-ray image. The radiopaque part is divided into at least a first radiopaque region, a second radiopaque region, and a third radiopaque region which are sequentially arranged each immediately after one another in the lengthwise direction of the wire body such that the second radiopaque region is positioned between the first and third radiopaque regions. The radiopaque member is located in each of the first, second and third radiopaque regions, and second radiopaque region possesses a lesser X-ray image producing capability than the first radiopaque region and the third radiopaque region. The lesser X-ray image producing capability of the second radiopaque region relative to the first radiopaque region being due at least in part to the radiopaque member in the second radiopaque region being arranged less densely than that the radiopaque member in the first radiopaque region, and that the X-ray producible radiopaque material in the resin coating layer in the second radiopaque region being less capable of forming an X-ray image than the X-ray producible radiopaque material in the resin coating layer in the first radiopaque region.

The X-ray producible radiopaque material in the resin coating is preferably particles of a metallic material or a metal oxide. According to one version, the radiopaque member is a helically wound coil that is more densely wound in the first radiopaque region than in the second radiopaque region. The coil is preferably formed from a single filamentous body extending from the first radiopaque region to the third radiopaque region. Alternatively, the radiopaque member comprises a plurality of ring-shaped members arranged in the lengthwise direction of the wire body, with adjacent ring-shaped members arranged more densely in the first radiopaque region than in the second radiopaque region.

It is desirable that the radiopaque member in the first and third radiopaque regions is arranged 3 to 7 times as densely as the radiopaque member in the second radiopaque region. It is also preferable for the content of the radiopaque material in the resin coating layer in the second radiopaque region to be less than 10% of the content of the radiopaque material in the resin coating layer in the first radiopaque region.

The first radiopaque region and the third radiopaque region should preferably be similar to each other in ability to form an X-ray image. Also, the first radiopaque region should be longer than the second radiopaque region, and the second radiopaque region should be equal to or longer than the third radiopaque region.

Preferably, the resin coating layer in the second radiopaque region should differ in color from that in either of the first radiopaque region and the third radiopaque region. The part of the wire body where the radiopaque part is arranged is preferably at least partly tapered in such a way that the outside diameter gradually decreases in the distal end direction. The radiopaque part is preferably in close contact with the wire body.

In accordance with another aspect, a guide wire comprises an elongated wire body and an X-ray producible radiopaque part. The elongated wire body possesses a distal end portion and extends in the lengthwise direction, with the radiopaque part located at the distal end portion of the wire body. The radiopaque part comprises a first radiopaque region, a second radiopaque region, and a third radiopaque region which are sequentially arranged each immediately after one another in the lengthwise direction of the wire body such that the second radiopaque region is positioned between the first and third radiopaque regions, and the first radiopaque region is located distally of the third radiopaque region. The second radiopaque region possesses a lesser X-ray image producing capability than the first radiopaque region and the third radiopaque region. The first radiopaque region possesses a length L1, the second radiopaque region possesses a length L2, and the third radiopaque region possesses a length L3, and $L1 \geq L2 \geq L3$.

Preferably, the ratio of L2/L1 is 0.1 to 0.7, the ratio of L3/L2 is 0.1 to 1, and the first radiopaque region and the third radiopaque region possess equal X-ray producing capabilities. In addition, the radiopaque part has a radiopaque member arranged around the wire body in the lengthwise direction of the wire body, wherein the radiopaque part comprises an X-ray producible metallic material in combination with a resin coating layer covering the radiopaque member and at least partly containing an X-ray producible radiopaque material.

It is desirable that the length L1 is 10 to 80 mm and the length L2 is 3 to 40 mm. In addition, the difference in capability of forming an X-ray image between the first radiopaque region and the second radiopaque region is preferably due to the fact that the radiopaque members in the second radiopaque region are arranged less densely than in the first radiopaque region. The difference in capability of forming an X-ray image between the first radiopaque region and the second radiopaque region can also be attributable to the fact that the resin coating layer in the second radiopaque region contains a lesser amount of radiopaque material than the resin coating layer in the first radiopaque region.

Further preferably, the difference in capability of forming an X-ray image between the first radiopaque region and the second radiopaque region should be due to the fact that the radiopaque member in the second radiopaque region is arranged less densely than in the first radiopaque region and that the resin coating layer in the second radiopaque region contains a less amount of radiopaque material than the resin coating layer in the first radiopaque region.

The radiopaque material should desirably be particles of a metallic material or a metal oxide. The content of the radiopaque material in the resin coating layer in the second radiopaque region should desirably be less than 10% of the content of the radiopaque material in the resin coating layer in the first radiopaque region and the third radiopaque region.

With the guide wire disclosed here, the radiopaque part is capable of forming an X-ray image with a varying degree of opaqueness depending on its positions (the first to third radiopaque regions). The difference in opaqueness produces a high contrast. This permits one to distinguish the distal part of the guide wire from other parts of the guide wire and to recognize at least the three regions in the distal part, when the guide wire is being inserted into the lumen of a living body by radioscopy. The recognition of the three regions permits one to accurately locate the guide wire being inserted into the lumen of a living body. For example, this permits one to prevent the guide wire from slipping off unexpectedly.

The first radiopaque region is longer than the second radiopaque region, and the second radiopaque region is equal to or longer than the third radiopaque region. This, in combination the radiopaque regions differing in opaqueness, permits one to accurately and rapidly operate the guide wire and to locate the position of the guide wire being inserted into the lumen of a living body, consequently, the guide wire can be advanced into the lumen of a living body adequately. The first radiopaque region (longest) which enters first the lumen helps one to distinguish it from other radiopaque regions. This permits one to accurately locate the guide wire.

The first radiopaque region may be longer than the second radiopaque region and the second radiopaque region may be equal to or longer than the third radiopaque region. This permits one to accurately locate the guide wire being inserted into the lumen of a living body, consequently, the guide wire can be advanced into the lumen of a living body adequately.

BRIEF DESCRIPTION OF THE DRAWING FIGURES

DETAILED DESCRIPTION

Figure 1:
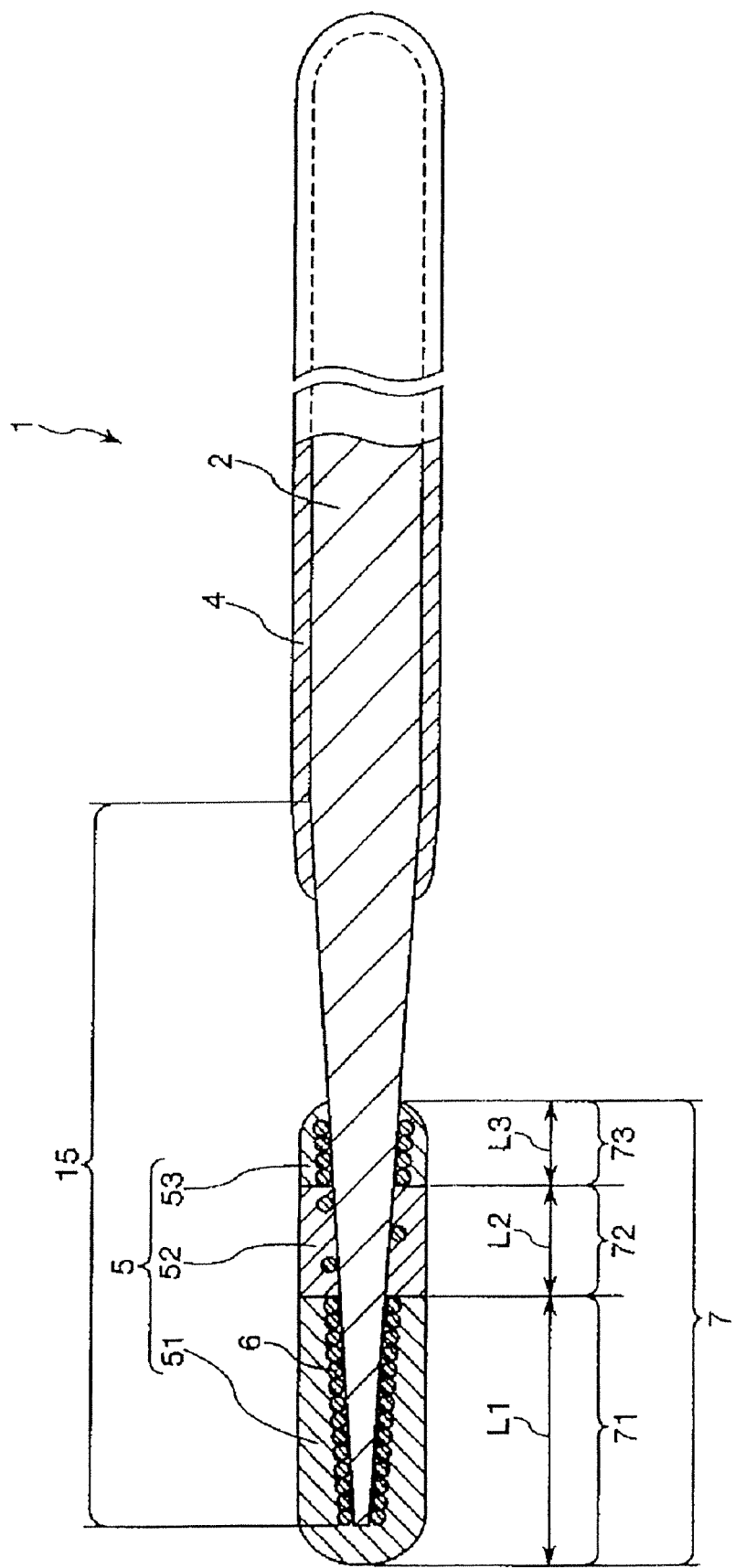
FIG. 1 is a longitudinal cross-sectional view of the guide wire according to a first embodiment disclosed here.

FIG. 1 illustrates, in longitudinal cross-section, a guide wire disclosed herein. For convenience from the standpoint of explanation, the right side in FIG. 1 is referred to as the "proximal portion" and the left side in FIG. 1 is referred to as the "distal end.". This same convention also applies to FIGS. 2-6. Also, to help illustrate aspects of the guide wire and for ease in understanding, the guide wire is schematically shown in FIG. 1 with a shortened length and exaggerated thickness. Therefore, the illustrated ratio of the thickness to the length differs from that associated with the actual guide wire. Once again, this observation also applies to FIGS. 2-6, The guide wire 1 shown in FIG. 1 is a catheter guide wire or a transendoscopic guide wire which, at the time of use, is inserted into the lumen of a catheter (or an endoscope). The guide wire is comprised of a wire body 2 which consists of a flexible or soft core wire (or an extended linear core). The wire body 2 has a round shape in cross-section.

According to this embodiment, the wire body 2 consists of one continuous core wire (i.e., an integrally formed one-piece core wire). However, the present invention also covers the wire body 2 consisting of two or more core wires (of identical or different materials) welded together.

The guide wire 1 should preferably possess an overall length of about 200 to 5000 mm, though the length is not specifically limited in that regard.

According to this embodiment, the wire body 2 consists of two parts or sections, a first part possessing a uniform outside diameter and the second part gradually tapering (i.e., gradually reducing) in outer diameter toward the distal end. The second part may taper in a manner other than gradually along its length. For example, the second part can be configured to taper in two or more steps. The wire body 2 shown in FIG. 1 has at its distal end configured so that it possesses one tapering part 15.

The tapering part 15 gradually decreases the flexural and torsional stiffness of the wire body (core) 2 in the direction toward the distal end. This makes the guide wire 1 flexible at its distal end, which improves safety, permits the guide wire to track the blood vessel relatively easily, and contributes to preventing the guide wire from bending. As discussed in more detail below, this tapering part 15 is also where the radiopaque part 7 is arranged.

The illustrated guide wire is constructed so that the tapering part 15 is at the distal end (a portion in the lengthwise direction) of the wire body 2. However, the tapering part 15 may extend over the entire length of the wire body 2. The tapering part 15 may decrease in outside diameter evenly or unevenly in the lengthwise direction. In other words, the angle of taper may be constant or variable along the tapering part. In the latter case, a steep taper and a mild taper may repeat themselves more than once.

The wire body 2 has a uniform outside diameter along its length from the proximal point of the tapering part 15 to the proximal end portion of the wire body 2.

The core wire of the wire body 2 may be formed from any of the following materials, without specific restrictions: stainless steel (such as SUS304, SUS303, SUS302, SUS316, SUS316L, SUS316J1, SUS316J1L, SUS405, SUS430, SUS434, SUS444, SUS429, SUS430F, and SUS302), piano wire, iron-cobalt alloy, carbon steel (including low-carbon and ultra low-carbon steels), mild steel, hard steel, ferroalloy (such as nickel steel, nickel-chromium steel, and nickel-chromium-molybdenum steel), and other alloys (such as cobalt alloy, titanium alloy, and nickel alloy). Of these examples, stainless steel is most desirable because of its higher strength and stiffness than the superelastic alloy mentioned later. It provides the guide wire 1 pushability and torque transmission performance.

The core wire of the wire body 2 may also be formed from any alloy which exhibits pseudoelasticity, such as a superelastic alloy.

A superelastic alloy is characterized by flexibility and elasticity (ability to recover itself from bending). Thus, when applied to the wire body 2, it makes the distal portion of the guide wire 1 sufficiently flexible and capable of restoration after bending. The resulting guide wire 1, therefore, is able to relatively easily track the intricately winding and bending of blood vessels. This leads to good steerability. In addition, because the wire body 2 is able to relatively easily recover itself from bending, the guide wire 1 is free of sustained bending (i.e., the guide wire does not maintain a bent shape) that adversely affects its steerability.

The pseudoelastic alloy includes those which give any stress-strain curve due to tensile force or those which may or may not have marked transformation temperatures (such As (austenite start temperature), Af (austenite finish temperature), Ms (martensite start temperature), Mf (martensite finish temperature). It includes any alloy which greatly deforms under stress and restores its original shape almost completely when stress is removed.

Some desirable examples of the superelastic alloy are listed below. Ni—Ti alloy containing 49 to 52 at % of Ni. Cu—Zn alloy containing 38.5 to 41.5 wt % of Zn. Cu—Zn—X alloy containing 1 to 10 wt % of X (where X is at least one species selected from Be, Si, Sn, Al, and Ga). Ni—Al alloy containing 36 to 38 at % of Al. Of these examples, the Ni—Ti alloy is most desirable. The superelastic alloy typified by the Ni—Ti alloy is superior in adhesion to the surface layer 4 mentioned later.

Cobalt alloy has a relatively high modulus of elasticity and an adequate elastic limit. Therefore, a cobalt alloy wire is superior in torque transmission performance and almost free of troubles such as buckling. No specific restrictions are imposed on the kind of cobalt alloy which can be employed so long as the alloy contains cobalt. Those alloys in which cobalt dominates (a Co-based alloy or an alloy which contains cobalt dominantly by weight percent) are desirable. Co—Ni—Cr alloys are most desirable. They will enhance the above-mentioned effect. Besides, because alloys of such compositions are high in modulus of elasticity, and can be cold formed even when they are conditioned to have a relatively high elastic limit, they permit the guide wire to be made thin while protecting it from buckling and they also impart good flexibility and stiffness necessary for the guide wire to be inserted into the desired position.

As mentioned above, the wire body 2 may consist of two or more core wires of different materials joined together. For example, it may consist of a first core wire (positioned at a distal portion and extending toward the distal end) and a second core wire (positioned at a proximal portion and extending toward the proximal end). In this case, the first core wire should preferably be made of superelastic alloy, particularly Ni—Ti alloy, and the second core wire should preferably be made of stainless steel (mentioned above). The boundary (or junction) between the first and second core wires may exist anywhere between the tapering part 15 and the proximal portion, at the proximal point of the tapering part 15, or anywhere in the tapering part 15.

The distal end of the wire body 2 (or the distal end of the first core wire) may have a shapeable part which is shapeable.

The wire body 2 may have its surface treated for good adhesion to the surface layer 4 (discussed later). The treatment includes surface roughening treatment, chemical treatment, and heat treatment.

As shown in FIG. 1, the guide wire 1 having the wire body 2 includes the radiopaque part 7 at its distal end. The radiopaque part 7 is adapted to produce an X-ray image (i.e., an X-ray producible radiopaque part 7). The radiopaque part 7 consists of the coil 6 (which is radiopaque) surrounding the wire body 2 and the resin coating layer 5 that covers the coil 6. The radiopaque part 7 is divided into three sections, namely the first radiopaque region 71, the second radiopaque region 72, and the third radiopaque region 73, which are arranged in that order in the lengthwise direction from the distal end. These three regions differ from one another in terms of the degree of opaqueness. They also differ from each other in terms of their length in the lengthwise direction of the wire body 2.

The radiopaque part 7 has its distal end rounded to contribute to the safety of the guide wire 1.

The coil 6 surrounding the distal end of the wire body 2 is a thin wire that helically winds around the wire body 2 in its circumferential and lengthwise directions. The coil 6 consists of a single wire that continues from the first radiopaque region 71 to the third radiopaque region 73. This structure imparts good flexibility to the radiopaque part 7, thereby contributing to safety and the ability to track the lumen. This structure also reduces the number of parts constituting the radiopaque part 7 and reduces the production cost of the guide wire 1. The coil 6 may be wound tightly, loosely, and tightly in the distal direction from the distal end toward the proximal end. That is, the coil may be wound so that the distal-most portion of the coil is tightly wound, followed by a portion that is loosely wound (less tightly wound than the distal-most portion), followed by a proximal-most portion of the coil that is tightly wound like the distal-most portion. The terms "tightly wound" and "loosely wound" as used here refer to the relative spacing of adjacent windings of the coil. Thus, the tightly wound coil in the first and third radiopaque regions 71, 73 is wound such that adjacent windings are closer (tighter) together, whereas the loosely wound coil in the second radiopaque region 72 is wound such that adjacent windings are relatively farther apart (looser). An advantage of this construction is that the radiopaque part 7 does not abruptly change in physical properties in its lengthwise direction.

The coil 6 is made of a metallic material selected from noble metals (such as gold and platinum) and alloys thereof (such as platinum-iridium alloy) and tungsten. Thus, the coil 6 makes the guide wire 1 opaque to X-rays (the coil 6 is made of an X-ray producible radiopaque material).

The coil 6 is formed in such a way that its inside surface is in close contact with the outside surface of the tapering part 15 of the wire body 2.

In this embodiment, the coil 6 is formed from a wire having a round cross section. However, the wire may have a square (or rectangular) cross-sectional shape or an elliptical cross-sectional shape.

The radiopaque part 7 contains the coating layer 5 that covers the coil 6. The coating layer 5 may be formed from any resin selected, without restrictions, from polyurethane, polyolefins (such as polyethylene, polypropylene, and ethylene-propylene copolymer), fluoroplastics (such as polytetrafluoroethylene), polyesters (such as polyethylene terephthalate), polyvinyl chloride, polyamide, polyimide, ethylene-vinyl acetate copolymer, ethylene-acrylonitrile-copolymer, ABS resin, AS resin, butadiene-styrene copolymer, polyisoprene, and polybutadiene. Preferable among them is a material such as polyurethane which is comparatively highly flexible because of its flexibility and superiority in adhesion to the wire 2.

The constituent of the coating layer 5 is partly incorporated with metal powder as a radiopaque material. That is, the coating layer 5 includes metal powder so that the coating layer 5 is made of an X-ray producible material. The metal powder may be tungsten or noble metal (such as gold and platinum), the former being preferable. The kind and content of the metal powder determine the opaqueness of the first to third radiopaque regions 71, 72, 73 of the radiopaque part 7.

The radiopaque material in the coating layer 5 should have a particle size of 0.5 to 4.0 μm, preferably 1.0 to 1.5 μm, though the particle size is not specifically limited in that regard.

The coating layer 5 may be a single-layer structure or a multi-layer structure.

The wire body 2 has its outside surface covered partly or entirely with the surface layer 4. The surface layer 4 shown in FIG. 1 covers the region of the wire body 2 from the proximal point of the tapering part 15 to the proximal portion of the wire body 2 (proximal-most end of the wire body 2). The surface layer 4 has multiple purposes. One purpose is to help make the guide wire 1 easily slidable with reduced friction, so that the guide wire 1 possesses improved steerability.

The surface layer 4 should preferably be formed from a fluoroplastic, which effectively reduces friction between the guide wire 1 and the inner wall of the catheter. This leads to improved slidability and steerability of the guide wire 1 in the catheter. In addition, reduced friction helps prevent the guide wire 1 from kinking and twisting which would otherwise occur when the guide wire 1 is moved or turned in the catheter.

The fluoroplastic which can be sued for the surface layer 4 includes, for example, polytetrafluoroethylene (PTFE), tetrafluoroethylene-perfluoroalkylvinyl ether copolymer (PFA), polychlorotrifluoroethylene (PCTFE), polyvinylidene fluoride (PVDF), polyvinyl fluoride (PVF), tetrafluoroethylene-hexafluoropropylene copolymer (FEP), and tetrafluoroethylene-ethylene copolymer (PETFE). They may be used alone or in combination with one another.

The guide wire 1 has its surface (at least in the region of its distal end) coated with a hydrophilic material, which when wetted reduces the friction of the guide wire 1. This results in the guide wire 1 possessing improved slidability and steerability.

The hydrophilic material includes, for example, cellulosic polymer, polyethylene oxide, methylvinyl ether-maleic anhydride copolymer, polyacrylamide, polyglycidyl methacrylate-dimethylacrylamide block copolymer (PGMA-DMAA), water-soluble nylon, polyvinyl alcohol, and polyvinylpyrrolidone.

The hydrophilic materials mentioned above usually absorb water or become moistened to reduce friction between the guide wire 1 and the inner wall of the catheter or endoscope. This produces the effect of improving the slidability and steerability of the guide wire 1.

As mentioned above, the radiopaque part 7 is divided into the first to third radiopaque regions 71, 72, 73. The second region 72 has the least opaqueness among the three regions. Since the first and third regions are of the same structure, the difference in opaqueness will be explained below with reference to the first region, it being understood that the same description applies to the third region 73.

As shown in FIG. 1, the coil 6 is wound more densely in the first radiopaque region 71 than in the second radiopaque region 72. In other words, the coil 6 is tightly wound in the first radiopaque region 71 and is loosely wound in the second radiopaque region 72.

Moreover, the coating layer 5 in the radiopaque part 7 varies in the content of the radiopaque material from one region to another. That is, the coating layer 52 (that portion of the coating layer 5 corresponding to the second radiopaque region 72) contains a lesser amount of radiopaque material than the more distally located coating layer 51 (that portion of the coating layer 5 corresponding to the first radiopaque region 71).

In this way, the radiopaque part 7 varies in opaqueness from the first radiopaque region 71 to the second radiopaque region 72 according to the winding pitch of the coil 6 and the content of the radiopaque material. Thus, the radiopaque part 7 has two regions (at both of its ends), where opaqueness is high, and one region (at middle), where opaqueness is low.

This construction of the radiopaque part 7 as discussed above produces a number of effects such as those discussed below. For example, the radiopaque part 7 as a whole is opaque to X-rays and yet it varies in opaqueness from one region to another. The first radiopaque region 71 is relatively more opaque, the second radiopaque region 72 is relatively less opaque compared to the first region 71 (and the third region 73), and the third region 73 is relatively more opaque. The difference in opaqueness produces a relatively high contrast. The highly contrasting opaqueness permits a user to distinguish the distal end (the radiopaque part 7) from the other part of the guide wire 1. Moreover, the difference in opaqueness permits one to recognize the three divided parts in the distal end of the guide wire 1. The second radiopaque region 72 enables one to identify (visually identify) the third radiopaque region 73 more certainly.

The radiopaque regions varying in opaqueness permit one to accurately locate the distal end and other parts of the guide wire 1 being inserted into the lumen (such as bile duct) of a living body by radioscopy. In other words, it makes it possible to determine how far the guide wire 1 has advanced, and so the guide wire can be adequately advanced into the lumen of a living body adequately. This prevents the guide wire 1 from unexpectedly moving from the desired position.

Depending upon the intensity of the X-rays, the results achieved by the guide wire construction here may not be produced if the radiopaque part 7 consists of the coil 6 or the radiopaque material alone.

According to known technology, it is necessary to fix the coil to the wire body with solder or adhesive. The resulting fixed part at which the coil is fixed to the wire body becomes stiffer than the other parts. Moreover, the coating layers, which contain more radiopaque material than the other coating layer, detrimentally influence the adhesion of the coil to the wire body, though this may also depend on the constituent of radiopaque material.

In the guide wire 1 disclosed here, however, the coating layer 72 of the radiopaque part 7 contains only a small quantity (or none) of radiopaque material and hence it is able to relatively firmly adhere to the coil 6 and the wire body 2 or it helps the entire coating layer 7 to be fixed to the coil 6 and the wire body 2. That is, radiopaque material in the coating layer 7 does not adversely effect the adhesion qualities in the same manner as mentioned above. In addition, the coating layers 71-73 are bonded together by mutual dissolution of resin materials, and they (as the entire coating layer 7) firmly fix to the coil 6 and the wire body 2. This eliminates the necessity of fixing the coil 6 with the above-mentioned fixing material, thereby preventing the distal end of the guide wire 1 from becoming stiffer. In other words, the distal end of the guide wire 1 remains relatively flexible.

Though not limited in this regard, the coil 6 in the first radiopaque region 71 should preferably be wound 3 to 7 times denser, preferably 4 to 7 times denser, than the coil 6 in the second radiopaque region 72.

The content (amount) of radiopaque material in the coating layer 52 should be less than 10%, preferably less than 5%, of that in the coating layer 51, though the guide wire is not necessarily limited in this regard. The content may be zero.

The radiopaque part 7 that produces a high contrast contributes to good steerability of the guide wire 1 inserted into the desired position in the lumen.

As mentioned above, the first and third radiopaque regions 71, 73 are identical or almost identical in structure, and consequently they produce the same or almost the same degree of contrast. This facilitates the fabrication of the radiopaque part 7.

As shown in FIG. 1, the first to third radiopaque regions 71, 72, 73 are arranged in descending order of length. Specifically, the length (L1) of the first radiopaque region 71 is longer than the length (L2) of the second radiopaque region 72, and the length (L2) of the second radiopaque region 72 is longer than the length (L3) of the third radiopaque region 73. When the guide wire 1 is inserted into the lumen of a living body, the first radiopaque region 71, which is longest, can surely be inserted and permits the guide wire 1 to be inserted deep enough to avoid slipping out. The second and third radiopaque regions 72, 73 serve as marks to lead the guide wire 1 to the desired position. The radiopaque regions differing in length and contrast help the rapid and accurate insertion under radioscopy.

The length (L1) of the first radiopaque region 71 should be 10 to 80 mm, preferably 30 to 70 mm. The length (L2) of the second radiopaque region 72 should be 3 to 40 mm, preferably 10 to 20 mm. The length (L3) of the third radiopaque region 73 should be 1 to 20 mm, preferably 3 to 10 mm.

The ratio of L2/L1 should be 0.1 to 0.7, preferably 0.2 to 0.6. The ratio of L3/L2 should be 0.1 to 1, preferably 0.2 to 1. These ratios are necessary to produce effects like those described above.

The coating layer 52 should preferably differ in color from the coating layers 51, 53. For example, the coating layer 52 should have a chromatic color (e.g., blue) and the coating layers 51, 53 should have an achromatic color (e.g., black). This color arrangement makes it easier to determine how far the guide wire 1 has advanced by way of an endoscope. Endoscopic observation in combination with radioscopy permits one to accurately locate the distal end of the guide wire 1.

The coloring of the coating layers 51-53 may be accomplished, for example, by incorporating pigments into the resin material constituting each coating layer.

The coating layers 51-53, which vary in the content of radiopaque material, though not limited in this regard, may be formed in the following manner.

The wire body 2, around which the coil 6 has been wound, is masked except for the parts where the coating layers 51, 53 are to be formed. The resin material containing a radiopaque material is applied, except for the masked part, to form the coating layers 51, 53.

The mask is removed, and the coating layers 51, 53 are masked. The resin material is applied, except for the masked parts, to form the coating layer 52. In this way the coating layers 51-53 are formed.

According to this embodiment, the wire body 2 is in contact with the inner surface of the coil 6. However, this is not essential. The tapering part 15 of the wire body 2 may simply pass through the coil 6 without contact with its inner surface.

According to this embodiment, the coil 6 is formed from a single continuous wire wound around the first to third radiopaque regions 71-73. However, this one-piece construction of the coil is not essential. The coil 6 may consist of three separate coils joined together. In this case, the coils at both ends may be made of different materials.

Figure 2:
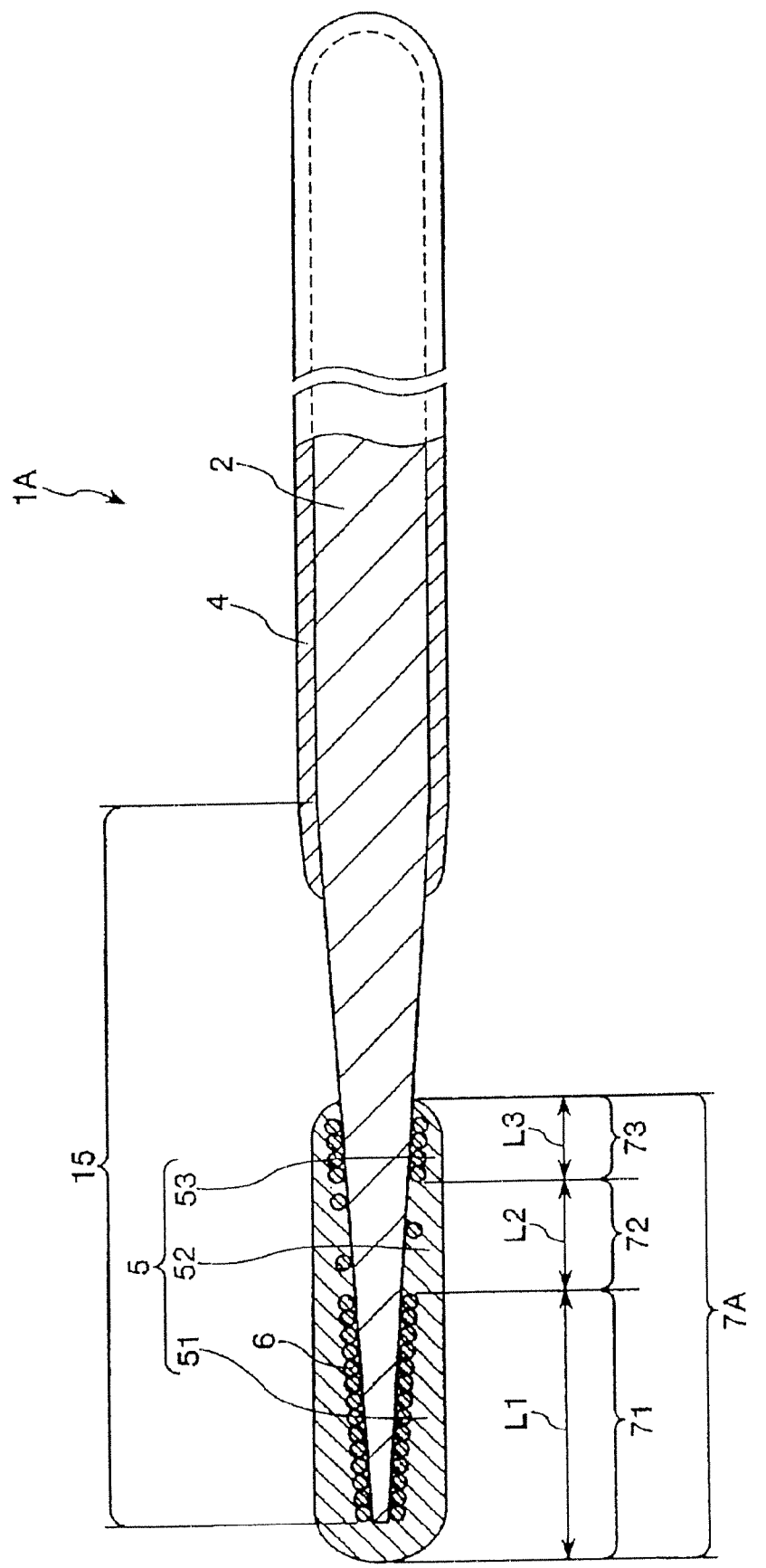
FIG. 2 is a longitudinal cross-sectional view of a second embodiment of the guide wire disclosed here.

FIG. 2 illustrates, in a longitudinal cross-sectional view, the guide wire according to a second embodiment. The description of the second embodiment will focus primarily upon difference between this embodiment and the first embodiment discussed above. Features in this second embodiment of the guide wire that are the same as those associated with the first embodiment are designated by like reference numerals, and a detailed discussion of such features will not be repeated. The second embodiment of the guide wire is identical with the first embodiment, except for the structure of the radiopaque part.

In the guide wire 1A shown in FIG. 2, the radiopaque part 7A comprises the coating layer 5 which consists of three coating layers 51, 52, 53. The coating layers 51, 52, 53 contain the same (inclusive of substantially the same) amount of radiopaque material which is uniformly distributed therein, and there is no difference in the amount of radiopaque material in the coating layers 51-53. Therefore, the first and second radiopaque regions 71, 72 differ in contrast only because the coil 6 is wound more densely in the first radiopaque region 71 than in the second radiopaque region 72.

The forgoing structure is effective in the case where it is desirable in radioscopy that the radiopaque part 7A should have a lower contrast than the radiopaque part 7 in the first embodiment.

Figure 3:
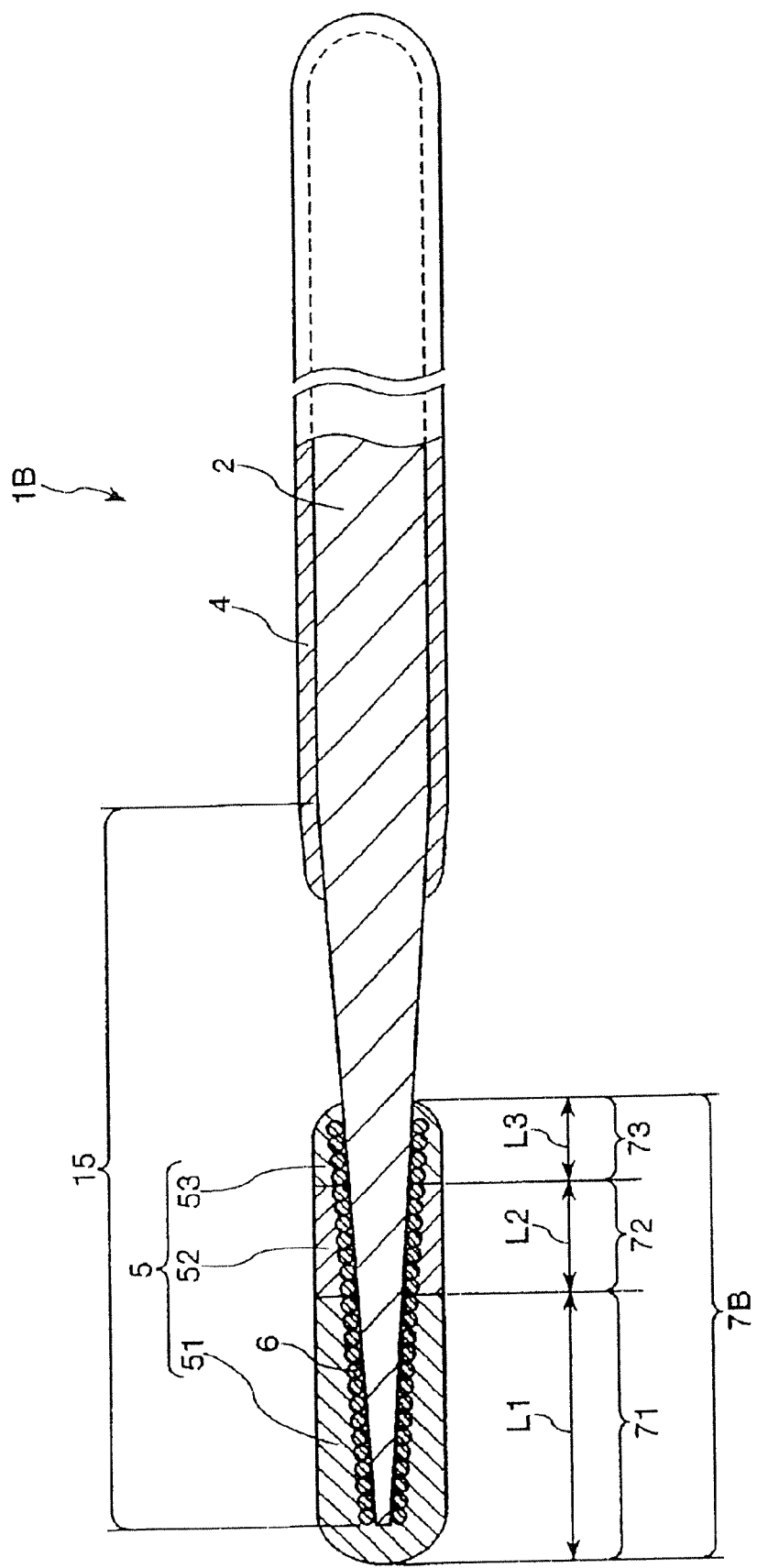
FIG. 3 is a longitudinal cross-sectional view of a third embodiment of the guide wire.

FIG. 3 illustrates, in a longitudinal cross-sectional view, the guide wire according to a third embodiment. The description of this third embodiment focuses primarily upon difference between this embodiment and the first embodiment discussed above. Features in the third embodiment of the guide wire that are the same as those associated with the previously described embodiments are designated by like reference numerals, and a detailed discussion of such features is not repeated. The third embodiment is identical with the first embodiment, except for the structure of the radiopaque part.

In the guide wire 1B shown in FIG. 3, the radiopaque part 7B comprises the coil 6 which is wound substantially uniformly (without pitch variation) throughout the first to third radiopaque regions 71, 72, 73. Thus, in the radiopaque part 7B, the difference in opaqueness between the first radiopaque region 71 and the second radiopaque region 72 is due mainly to the fact that the coating layer 52 contains a lesser amount of radiopaque material than the coating layer 51.

The guide wire shown in FIG. 3 is effective in situations where, for example, it is desirable during radioscopy that the radiopaque part 7B should have a lower contrast than the radiopaque part 7 in the guide wire of the first embodiment.

Figure 4:
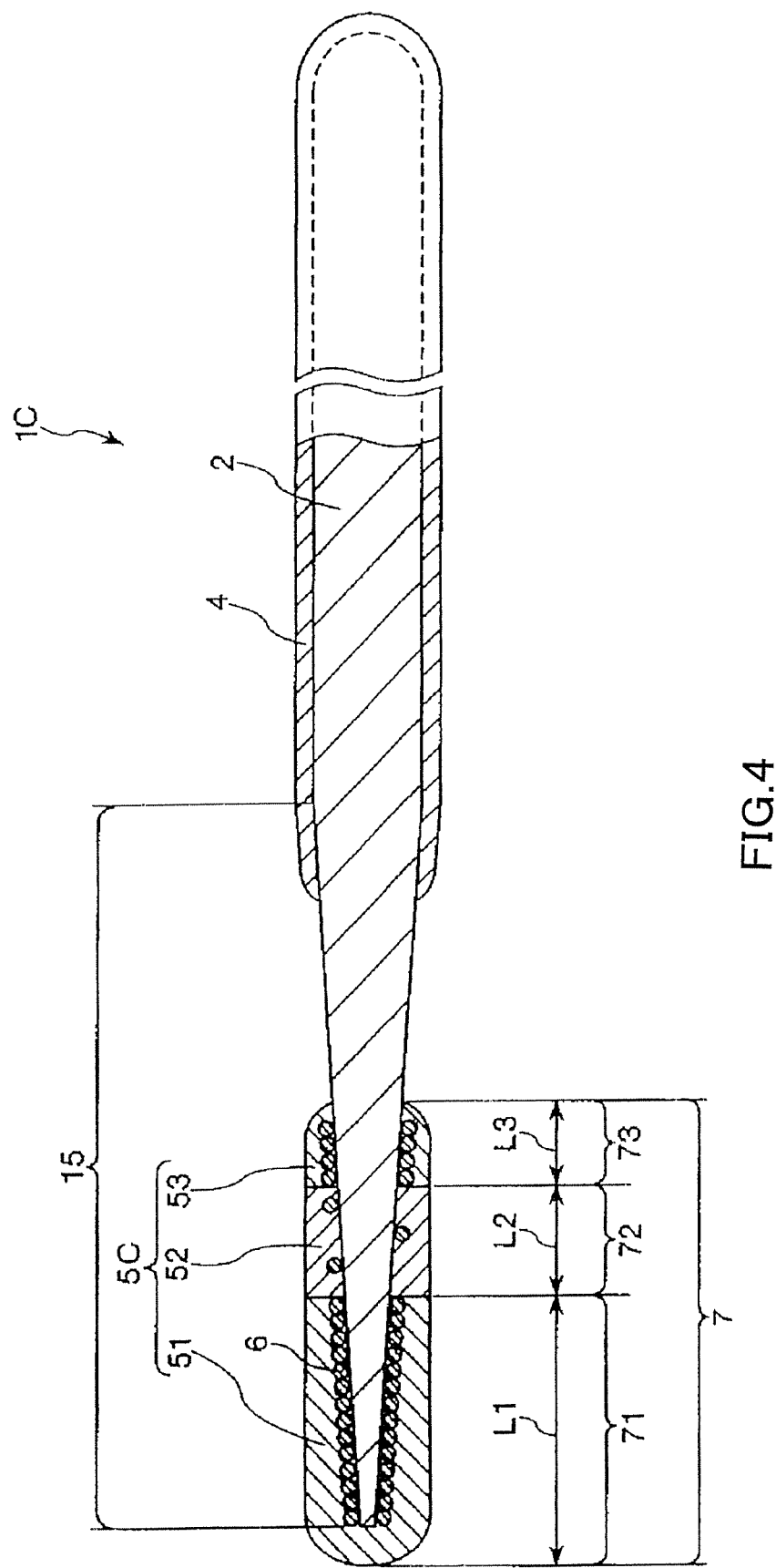
FIG. 4 is a longitudinal cross-sectional view of a fourth embodiment of the guide wire.

FIG. 4 illustrates, in a longitudinal cross-sectional view, the guide wire according to a fourth embodiment. The description of this fourth embodiment focuses primarily upon difference between this embodiment and the first embodiment discussed above. Features in the fourth embodiment of the guide wire that are the same as those associated with the previously described embodiments are designated by like reference numerals, and a detailed discussion of such features is not repeated. The fourth embodiment of the guide wire is identical to the first embodiment of the guide wire, except for the structure of the resin coating layer.

The guide wire 1C shown in FIG. 4 includes the coating layers 51, 52, 53 each containing the same amount (inclusive of substantially the same amount) of radiopaque material. However, the radiopaque material in the coating layer 52 is poorer in opaqueness than that in the coating layers 51, 53. The difference in opaqueness and the difference in the winding pitch of the coil 6 produce a synergistic effect of distinguishing between the first radiopaque region 71 and the second radiopaque region 72. Therefore, as in the first embodiment, the radiopaque part 7 produces a good contrast in radioscopy. On account of the radiopaque part 7 which produces a good contrast and has the radiopaque regions varying in length, it is possible to accurately locate the guide wire 1C in the lumen of a living body.

The coating layers 51, 52 can be made to possess different degrees of opaqueness by incorporating in them a radiopaque material differing in composition. For example, the radiopaque material in the two layers may be tungsten and bismuth sulfide, respectively, or tungsten and barium sulfide, respectively.

Figure 5:
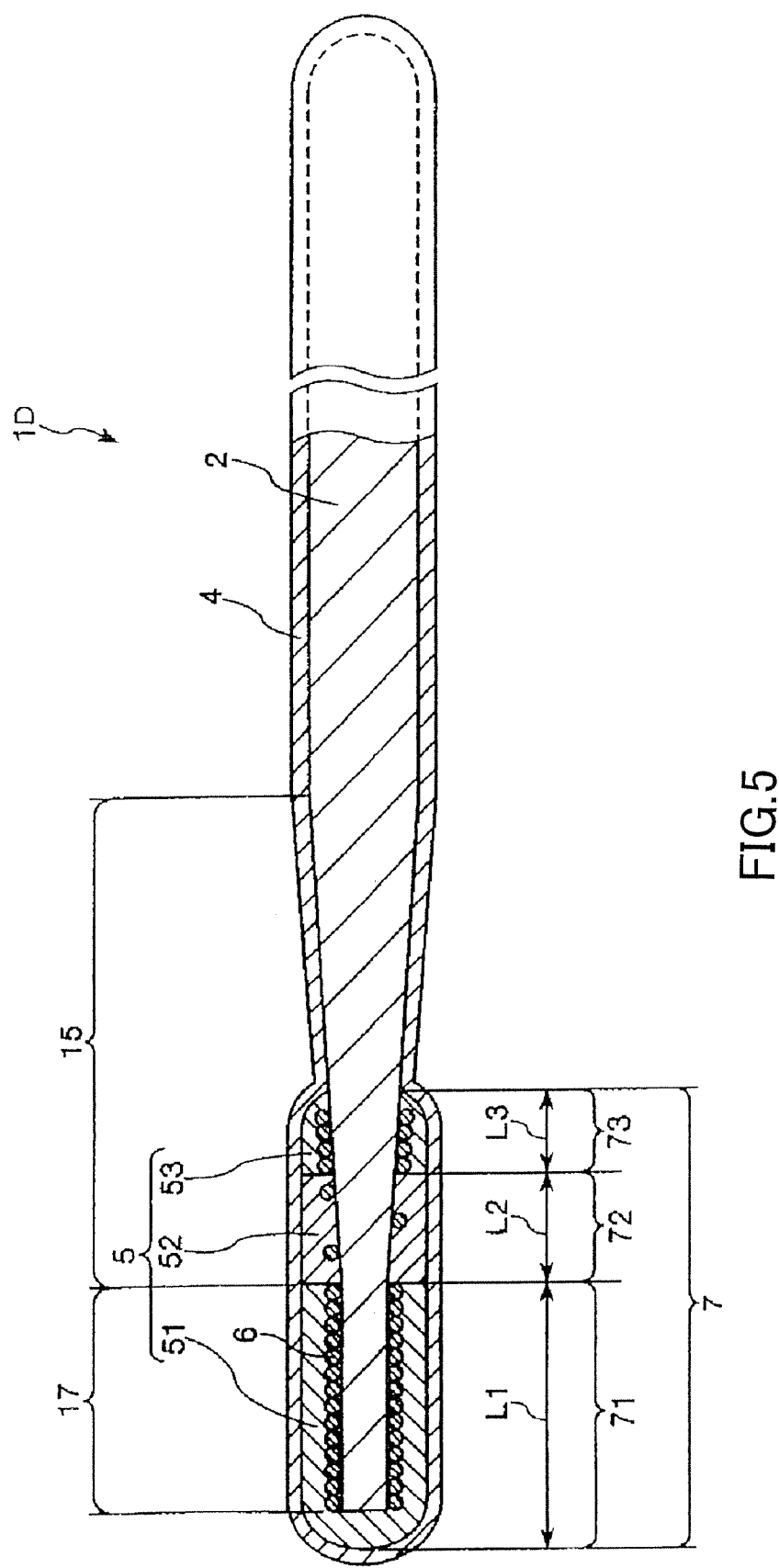
FIG. 5 is a longitudinal cross-sectional view of the guide wire according to a fifth embodiment.

FIG. 5 illustrates, in a longitudinal cross-sectional view, a fifth embodiment of the guide wire disclosed here. The description of this fifth embodiment focuses primarily upon difference between this embodiment and the first embodiment discussed above. Features in the fifth embodiment of the guide wire that are the same as those associated with the previously described embodiments are designated by like reference numerals, and a detailed discussion of such features is not repeated. The fifth embodiment of the guide wire is identical to the first embodiment except for the shape of the distal end of the wire body.

The guide wire 1D shown in FIG. 5 includes the wire body 2. The distal end part 17 of the wire body 2 possesses a uniform outside diameter and extends from the distal end of the tapering part 15 to the distal end (distal-most end) of the wire body 2. This structure makes the distal end of the wire body 2 gradually decrease in stiffness in the direction toward the distal end. As a result, the guide wire 1D possesses good flexibility at its distal end and is able to relatively easily track the blood vessel without bending, which leads to greater safety.

The radiopaque part 7 is formed to extend along the part 17 (which has a uniform outside diameter) and a portion of the tapering part 15. In other words, the radiopaque part 7 is coextensive with the part 17 and a distal end portion of the tapering part 15. In the illustrated embodiment, the distal end portion of the radiopaque part 7 extends slightly beyond the distal end of the part 17. The part 17 consists of the first, second and third radiopaque regions 71, 72, 73, though in the illustrated embodiment the distal end of the region 71 extends distally beyond the distal end of the part 17. The first radiopaque region 71 is in the part 17, and the second and third radiopaque regions 72, 73 are in the tapering part 15.

In the embodiment shown in FIG. 5, the part 17 is formed at the distal end of the wire body 2; however, it may also be formed in any part of the wire body 2 (for example, in the middle of the tapering part 15).

The surface layer 4 in the FIG. 5 embodiment covers the guide wire 1D entirely (from the distal end to the proximal portion). The surface layer 4 reduces the friction (sliding resistance) of the guide wire 1 and improves slidability, which contributes to the steerability of the guide wire 1.

Figure 6:
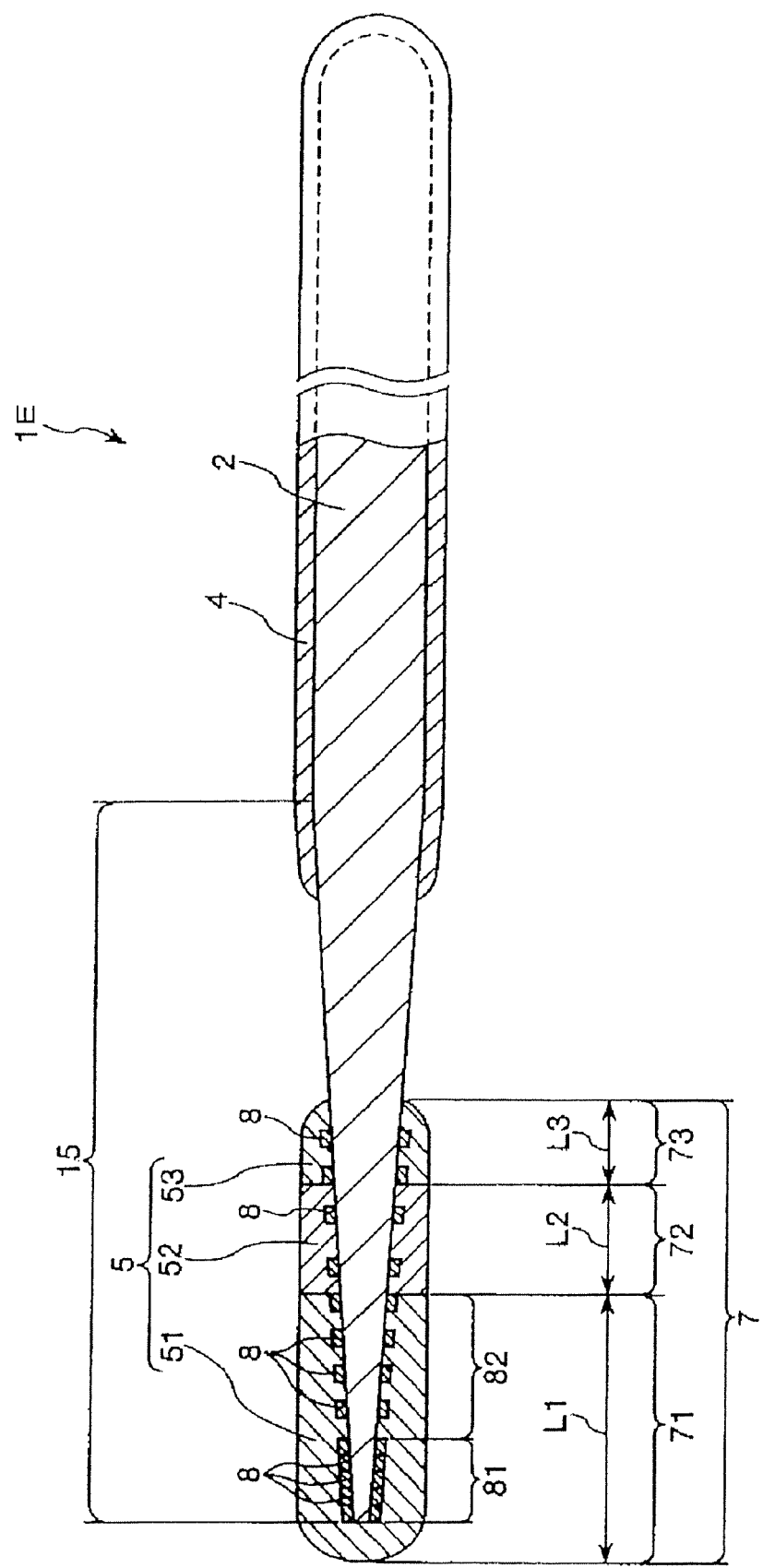
FIG. 6 is a longitudinal cross-sectional view of the guide wire according to a sixth embodiment.

FIG. 6 illustrates, in a longitudinal cross-sectional view, a further embodiment of the guide wire disclosed here. The description of this sixth embodiment of the guide wire focuses primarily upon difference between this embodiment and the first embodiment discussed above. Features in the sixth embodiment of the guide wire that are the same as those associated with the previously described embodiments are designated by like reference numerals, and a detailed discussion of such features is not repeated. The sixth embodiment is identical with the first embodiment except for the structure of the radiopaque member.

The guide wire 1E shown in FIG. 6 has ring-shaped (annular) members 8 which are opaque to X-rays. The ring-shaped members are arranged in the lengthwise direction of the wire body 2 and positioned along the tapering part 15 of the wire body 2. The inner circumferential surface of the ring-shaped members 8 is intimately in contact with the outer circumferential surface of the wire body 2.

The ring-shaped members 8 are arranged more closely (i.e., are positioned closer to one another in the axial direction), on average, in the first and third radiopaque regions 71, 73 than in the second radiopaque region 72. Moreover, the first radiopaque region 71 consists of several subsections. In the illustrated embodiment, the first radiopaque region 71 consists of two subsections 81, 82. In the subsection 81, the adjacent ring-shaped members 8 are in contact with one another. In the subsection 82, located between the subsection 81 and the second radiopaque region 72, the adjacent ring-shaped members 8 are spaced from one another. The subsection 81 is closer to the distal end than the subsection 82.

The guide wire 1E is constructed so that the ring-shaped members are arranged at intervals that vary from the first radiopaque region 71 to the second radiopaque region 72. This difference in intervals combined with the difference in the content of radiopaque material makes an apparent difference in opaqueness between the first radiopaque region 71 and the second radiopaque region 72. Thus the radiopaque part 7 produces a good contrast as in the first embodiment. Owing to the radiopaque part 7 excelling in opaqueness and the radiopaque part 7 consisting of radiopaque regions differing in length, the guide wire 1E makes it possible to accurately locate its position by radioscopy at the time of its insertion into the lumen of a living body.

The ring-shaped members 8 functioning as the radiopaque members in the guide wire 1E can be easily arranged at varying intervals. The ring-shaped members 8 may be formed from any material, which includes such material as used for the coil 6 in the first embodiment.

In this embodiment, the ring-shaped members 8 have a square or rectangular cross-section. However, the ring-shaped members 8 can possess a round or elliptical cross-sectional shape.

In the foregoing, the guide wire disclosed here has been described with reference to several illustrated embodiments. However, the invention is not limited to the illustrated and described embodiments. Constituents of the guide wire may be replaced by those which have the same or similar function, or may be modified with additional elements.

Each of the disclosed embodiments may have any two or more structures (features) in combination selected from the foregoing embodiments.

The guide wire which has been discussed here is not limited to one used for transendoscopic technique. For example, it can also be used for therapy of CTO (chromic total occlusion) and angiography and PTCA (Percutaneous Transluminal Coronary Angioplasty).

According to the foregoing embodiments, the radiopaque part has three radiopaque regions. However, the guide wire can also be constructed to include one or two additional regions next to the third radiopaque region. In this case, the adjacent radiopaque regions should preferably differ in opaqueness from one another.

Embodiments of the guide wire illustrated in the drawing figures show the second radiopaque region being longer than the third radiopaque region. However, both regions may have the same length. Also, in the disclosed embodiments, the radiopaque part has the radiopaque members and the coating layer. However, either of them may be omitted. Additionally, the first and third radiopaque regions are described as having the same degree (inclusive of approximately the same degree) of opaqueness. However, the first region may have a higher or lower degree of opaqueness than the third region.

As discussed above, the coating layer contains metal powder as a radiopaque material. However, the metal powder may be replaced by any metal oxide power opaque to X-rays. The metal oxide powder includes, for example, barium sulfide, bismuth oxide, and barium carbonate. Of those, barium sulfide and the bismuth oxide are preferable. More than one kind of radiopaque material may be used in combination. For example, the coating layer in the first and third radiopaque regions may contain tungsten power (metal powder) as a radiopaque material and the coating layer in the second radiopaque region may contain barium sulfate powder (metal oxide powder) as a radiopaque material.

The principles, embodiments and modes of operation of the guide wire have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Various modifications, combinations, sub-combinations and alterations may occur, and still be within the scope of the claims including equivalents thereof, depending on requirements and other factors. Accordingly, it is expressly intended that all such variations, changes, modifications and equivalents which fall within the spirit and scope of the present invention as defined in the claims, be embraced thereby.

What is claimed is:

1. A guide wire comprising:

an elongated wire body and an X-ray image producible radiopaque part, the elongated wire body possessing a distal end portion and extending in a lengthwise direction, the elongated wire body possessing an outer surface, the radiopaque part being located at the distal end portion of the wire body;

the radiopaque part comprising a radiopaque member composed of an X-ray image producible metallic material which is adapted to produce an X-ray image under radioscopy, the radiopaque member being arranged outside the wire body and in the lengthwise direction of the wire body;

the radiopaque part also comprising a resin coating layer covering the radiopaque member, at least a part of the resin coating layer covering the radiopaque member containing X-ray image producible radiopaque metallic particles adapted to produce an X-ray image under radioscopy;

the radiopaque part being divided into at least a first radiopaque region, a second radiopaque region, and a third radiopaque region which are sequentially arranged each immediately after one another in the lengthwise direction of the wire body such that the second radiopaque region is positioned between the first and third radiopaque regions;

the radiopaque member being located in each of the first, second and third radiopaque regions;

the second radiopaque region possessing a lesser X-ray image producing capability than the first radiopaque region and the third radiopaque region;

the lesser X-ray image producing capability of the second radiopaque region relative to the first radiopaque region being due at least in part to the radiopaque member in the second radiopaque region being arranged less densely than that the radiopaque member in the first radiopaque region, and the resin coating layer in the second radiopaque region containing a lesser amount of the X-ray image producible radiopaque material than the resin coating layer in the first radiopaque region, the radiopaque member in the second radiopaque region that is arranged less densely including axially adjacent helical windings that are axially spaced apart from one another so that a gap exists between the axially adjacent helical windings;

the first radiopaque region including a distal most portion of the radiopaque member, and the radiopaque member in the first radiopaque region comprising a helical winding in which axially adjacent helical windings are in direct contact with one another, wherein the helical winding directly contacts the elongated wire body;

the resin coating layer comprising a more distally located coating layer corresponding to the first radiopaque region so that the more distally located coating layer is the part of the resin coating layer located in the first radiopaque region, a more proximally located coating layer corresponding to the third radiopaque region so that the more proximally located coating layer is the part of the resin coating layer located in the third radiopaque region, and an intermediately located coating layer corresponding to the second radiopaque region so that the intermediately located coating layer is the part of the resin coating layer located in the second radiopaque region, the intermediately located coating layer containing a lesser amount of the X-ray producible radiopaque material than the more distally located coating layer, and the intermediately located coating layer containing a lesser amount of the X-ray producible radiopaque material than the more proximally located coating layer, the intermediately located coating layer filling the gaps between the axially adjacent helical windings and directly contacting the outer surface of the elongated wire body.

2. The guide wire as defined in claim 1, wherein the X-ray image producible radiopaque metallic particles comprise powder particles.

3. The guide wire as defined in claim 2, wherein the radiopaque member is a helically wound coil that is more densely wound in the first radiopaque region than in the second radiopaque region, the helically wound coil in the second radiopaque region and in the third radiopaque region directly contacting a tapering outer surface of the elongated wire body whose outer diameter tapers from a larger outer diameter in the third radiopaque region to a smaller outer diameter in the second radiopaque region.

4. The guide wire as defined in claim 3, wherein the coil is formed from a single filamentous body extending from the first radiopaque region to the third radiopaque region.

5. The guide wire as defined in claim 1, wherein the radiopaque member is a helically wound coil that is more densely wound in the first radiopaque region than in the second radiopaque region, the helically wound coil in the second radiopaque region and in the third radiopaque region directly contacting a tapering outer surface of the elongated wire body whose outer diameter tapers from a larger outer diameter in the third radiopaque region to a smaller outer diameter in the second radiopaque region.

6. The guide wire as defined in claim 5, wherein the coil is formed from a single filamentous body extending from the first radiopaque region to the third radiopaque region.

7. The guide wire as defined in claim 1, wherein the radiopaque member comprises a plurality of ring-shaped members arranged in the lengthwise direction of the wire body, and adjacent ring-shaped members are arranged more densely in the first radiopaque region than in the second radiopaque region.

8. The guide wire as defined in claim 1, wherein:
the more distally located coating layer possesses a length $L1$, the more proximally located coating layer possesses a length $L2$, and the intermediately located coating layer possesses a length $L3$;
$L1 \geq L2 \geq L3$;
$L2/L1$ is 0.2-0.6; and
the amount of radiopaque material in the intermediately located coating layer is less than 10% the amount of radiopaque material in the more distally located coating layer.

9. The guide wire as defined in claim 1, wherein:
the more distally located coating layer possesses a length $L1$, the more proximally located coating layer possesses a length $L2$, and the intermediately located coating layer possesses a length $L3$;
$L1 \geq L2 \geq L3$;
$L2/L1$ is 0.1-0.7; and
the amount of radiopaque material in the intermediately located coating layer is less than 5% the amount of radiopaque material in the more distally located coating layer.

10. The guide wire according to claim 1, wherein the resin coating layer in the first radiopaque region has a first color, the resin coating layer in the second radiopaque region has a second color and the resin coating layer in the third radiopaque region has a third color, and wherein the second color is different from both the first color and the third color.

11. A guide wire comprising:
an elongated wire body and an X-ray image producible radiopaque part, the elongated wire body possessing a distal end portion and extending in a lengthwise direction, the radiopaque part being located at the distal end portion of the wire body;
the radiopaque part comprising a radiopaque member composed of an X-ray image producible metallic material which is adapted to produce an X-ray image under radioscopy, the radiopaque member being arranged outside the wire body and in the lengthwise direction of the wire body;
the radiopaque part also comprising a resin coating layer covering the radiopaque member, at least a part of the resin coating layer covering the radiopaque member containing X-ray image producible radiopaque metallic particles adapted to produce an X-ray image under radioscopy;
the radiopaque part being divided into at least a first radiopaque region, a second radiopaque region, and a third radiopaque region which are sequentially arranged each immediately after one another in the lengthwise direction of the wire body such that the second radiopaque region is positioned between the first and third radiopaque regions;
the radiopaque member being located in each of the first, second and third radiopaque regions;
the second radiopaque region possessing a lesser X-ray image producing capability than the first radiopaque region and the third radiopaque region;
the lesser X-ray image producing capability of the second radiopaque region relative to the first radiopaque region being due at least in part to the radiopaque member in the second radiopaque region being arranged less densely than the radiopaque member in the first radiopaque region;
the X-ray image producible radiopaque material in the resin coating layer in the second radiopaque region being less capable of forming an X-ray image than the X-ray image producible radiopaque material in the resin coating layer in the first radiopaque region;
the first radiopaque region including a distal most portion of the radiopaque member, and the radiopaque member in the first radiopaque region comprising a helical winding in which axially adjacent helical windings are in direct contact with one another, wherein the helical winding directly contacts the elongated wire body;
the resin coating layer comprising a more distally located coating layer corresponding to the first radiopaque region so that the more distally located coating layer is the part of the resin coating layer located in the first radiopaque region, a more proximally located coating layer corresponding to the third radiopaque region so that the more proximally located coating layer is the part of the resin coating layer located in the third radiopaque region, and an intermediately located coating layer corresponding to the second radiopaque region so that the intermediately located coating layer is the part of the resin coating layer located in the second radiopaque region, the intermediately located coating layer containing a lesser amount of the X-ray producible radiopaque material than the more distally located coating layer, and the intermediately located coating layer containing a lesser amount of the X-ray producible radiopaque material than the more proximally located coating layer;

wherein the more distally located coating layer has a first color, the intermediately located coating layer has a second color and the more proximally located coating layer has a third color; and the second color is different from both the first color and the third color.

12. The guide wire as defined in claim 11, wherein the X-ray image producible radiopaque metallic particles comprise powder particles.

13. The guide wire as defined in claim 11, wherein the radiopaque member is a helically wound coil that is more densely wound in the first radiopaque region than in the second radiopaque region, the helically wound coil in the second radiopaque region and in the third radiopaque region directly contacting a tapering outer surface of the elongated wire body whose outer diameter tapers from a larger outer diameter in the third radiopaque region to a smaller outer diameter in the second radiopaque region.

14. The guide wire as defined in claim 13, wherein the coil is formed from a single filamentous body extending from the first radiopaque region to the third radiopaque region.

15. The guide wire as defined in claim 11, wherein the radiopaque member comprises a plurality of ring-shaped members arranged in the lengthwise direction of the wire body, and adjacent ring-shaped members are arranged more densely in the first radiopaque region than in the second radiopaque region.

16. The guide wire according to claim 11, wherein a boundary exists between the axially adjacent helical windings that are in contact with one another in the first radiopaque region, wherein the more distally located coating layer containing the X-ray image producible radiopaque metallic particles covers all of the axially adjacent helical windings that are in contact with one another in the first radiopaque region and also covers all of the boundaries between the axially adjacent helical windings that are in contact with one another in the first radiopaque region.

17. A guide wire comprising:
an elongated wire body and an X-ray image producible radiopaque part, the elongated wire body possessing a distal end portion and extending in a lengthwise direction, the radiopaque part being located at the distal end portion of the wire body;
the radiopaque part comprising a first radiopaque region possessing a distal-most end and a proximal-most end, a second radiopaque region possessing a distal-most end and a proximal-most end, and a third radiopaque region possessing a distal-most end and a proximal-most end;
the first radiopaque region, the second radiopaque region and the third radiopaque region being sequentially arranged each immediately after one another in the lengthwise direction of the wire body such that the distal-most end of the second radiopaque region follows immediately after the proximal-most end of the first radiopaque region and the distal-most end of the third radiopaque region follows immediately after the proximal-most end of the second radiopaque region, and the first radiopaque region is located distally of the third radiopaque region;

the second radiopaque region possessing a lesser X-ray image producing capability than the first radiopaque region and the third radiopaque region;

the first radiopaque region possessing a length L1 measured between the distal-most end of the first radiopaque region and the proximal-most end of the first radiopaque region, the second radiopaque region possessing a length L2 measured between the distal-most end of the second radiopaque region and the proximal-most end of the second radiopaque region, and the third radiopaque region possessing a length L3 measured between the distal-most end of the third radiopaque region and the proximal-most end of the third radiopaque region, and $L1 \geq L2 \geq L3$;

wherein the radiopaque part comprises a radiopaque member arranged around the wire body in the lengthwise direction of the wire body, and X-ray image producible radiopaque metallic particles incorporated within a resin coating layer covering the radiopaque member;

the first radiopaque region including a distal most portion of the radiopaque member, and the radiopaque member in the first radiopaque region comprising a helical winding in which adjacent helical windings are in direct contact with one another, wherein the helical winding directly contacts the elongated wire body;

a proximal-most portion of the radiopaque member being located in the third radiopaque region;

the resin coating layer comprising a more distally located coating layer corresponding to the first radiopaque region so that the more distally located coating layer is the part of the resin coating layer located in the first radiopaque region, a more proximally located coating layer corresponding to the third radiopaque region so that the more proximally located coating layer is the part of the resin coating layer located in the third radiopaque region, and an intermediately located coating layer corresponding to the second radiopaque region so that the intermediately located coating layer is the part of the resin coating layer located in the second radiopaque region, the intermediately located coating layer containing a lesser amount of the X-ray producible radiopaque material than the more distally located coating layer, and the intermediately located coating layer containing a lesser amount of the X-ray producible radiopaque material than the more proximally located coating layer.

18. The guide wire as defined in claim 17, wherein the ratio of L2/L1 is 0.1 to 0.7.

19. The guide wire as defined in claim 17, wherein the ratio of L3/L2 is 0.1 to 1.

20. The guide wire as defined in claim 17, wherein the first radiopaque region and the third radiopaque region possess equal X-ray image producing capabilities.

21. The guide wire as defined in claim 17, wherein the X-ray image producible metallic particles comprise powder particles.

* * * * *